(12) United States Patent
Goodman et al.

(10) Patent No.: US 6,339,961 B1
(45) Date of Patent: Jan. 22, 2002

(54) ULTRASONIC DETECTING LUBRICATION APPARATUS WITH ACOUSTICALLY ISOLATED TRANSDUCER

(75) Inventors: Mark A Goodman, Cortlandt Manor; William Bishop, Pleasantville; John R. Zeno, deceased, late of New York, all of NY (US); by Linda Mabbs-Zeno, executrix, Alexandria, VA (US)

(73) Assignee: UE Systems, Inc., Alexandria, VA (US)

( * ) Notice: Subject to any disclaimer, the term of this patent is extended or adjusted under 35 U.S.C. 154(b) by 0 days.

(21) Appl. No.: 09/521,306

(22) Filed: Mar. 9, 2000

Related U.S. Application Data

(60) Continuation-in-part of application No. 09/028,554, filed on Feb. 24, 1998, which is a division of application No. 08/749,910, filed on Nov. 15, 1996, now Pat. No. 5,955,670.

(51) Int. Cl.$^7$ .......................... G01N 29/12; G01N 29/14
(52) U.S. Cl. ............................. 73/593; 73/660; 73/644; 184/105.2; 184/108
(58) Field of Search ........................... 73/593, 660, 658, 73/587, 644; 184/108, 105.1, 105.2, 105.3, 6.1, 6.4

(56) References Cited

U.S. PATENT DOCUMENTS

| | | | |
|---|---|---|---|
| 3,674,112 A | | 7/1972 | Roberts ...................... 184/6.1 |
| 3,952,566 A | | 4/1976 | Jacobson ....................... 73/10 |
| 4,038,866 A | * | 8/1977 | Johnson ......................... 73/593 |
| 4,287,581 A | | 9/1981 | Neale, Sr. .................... 367/135 |
| 4,316,115 A | * | 2/1982 | Wilson et al. ............... 310/327 |
| 4,416,145 A | | 11/1983 | Goodman et al. ............ 73/40.5 |
| 4,635,042 A | | 1/1987 | Andrews .................... 340/605 |
| 4,785,659 A | | 11/1988 | Rose et al. ................... 73/40.5 |
| 4,800,512 A | | 1/1989 | Busch .................... 364/551.01 |
| 4,823,600 A | | 4/1989 | Biegel et al. .................. 73/592 |
| 4,987,769 A | | 1/1991 | Peacock et al. ............... 73/49.7 |
| 4,998,439 A | * | 3/1991 | Shepard ......................... 73/592 |
| 5,080,195 A | | 1/1992 | Mizumoto et al. ........... 184/6.4 |
| 5,089,997 A | | 2/1992 | Pecukonis .................... 367/135 |
| 5,140,858 A | | 8/1992 | Nishimoto et al. ............ 73/587 |
| 5,350,040 A | | 9/1994 | Gribble .................... 184/105.2 |
| 5,432,755 A | | 7/1995 | Komninos ................... 367/135 |
| 5,691,707 A | | 11/1997 | Smith et al. ................. 340/682 |
| 5,955,670 A | | 9/1999 | Goodman ...................... 73/592 |
| 6,122,966 A | * | 9/2000 | Goodman et al. ............. 73/593 |

OTHER PUBLICATIONS

UVLM, Inc., "Ultra-Vibe Lubrication Monitor," Undated Brochure, (Centralia, Washington).

UVLM, Inc., "Your bearings are trying to tell you something . . . ", Aug. 18, 1997 Web Site, (http://www.uv-lm.com/).

* cited by examiner

*Primary Examiner*—Hezron Williams
*Assistant Examiner*—Rose M. Miller
(74) *Attorney, Agent, or Firm*—Darby & Darby

(57) ABSTRACT

An apparatus for detecting ultrasonic energy generated by a mechanical device and for applying lubricant to the device is presented. The apparatus includes a lubrication tool, such as a grease gun, which has a lubrication delivery element for delivering lubrication to the mechanical device. An ultrasonic transducer is contained in a housing which is removably attached to the outside of the lubrication delivery element. The housing is configured to acoustically isolate the transducer from the lubrication tool. An acoustic waveguide depending from the housing is provided to carry ultrasonic energy from the device to the transducer when the lubrication tool is applied to the device. An electrical circuit, which may be attached to the lubrication device, produces an output signal which indicates the magnitude of detected ultrasonic energy.

23 Claims, 8 Drawing Sheets

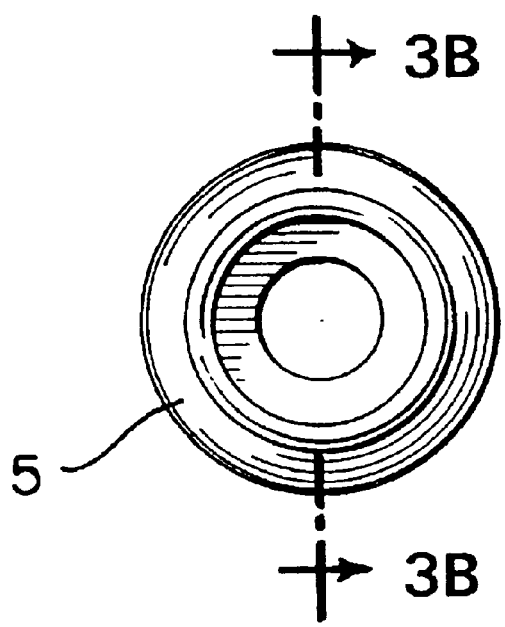
FIG. 3A
FIG. 3B
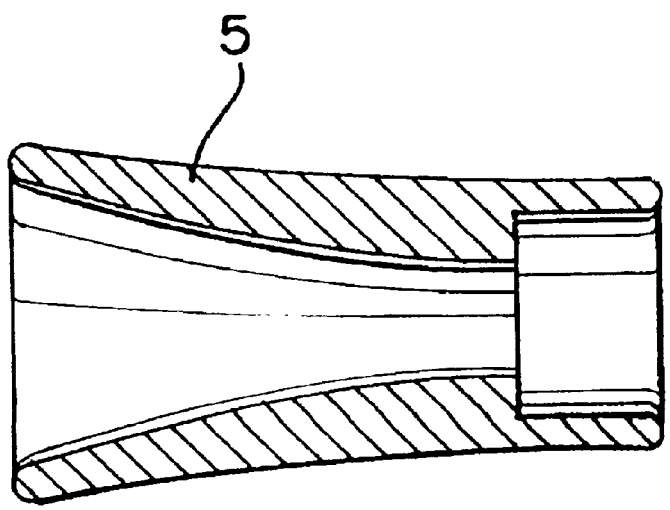

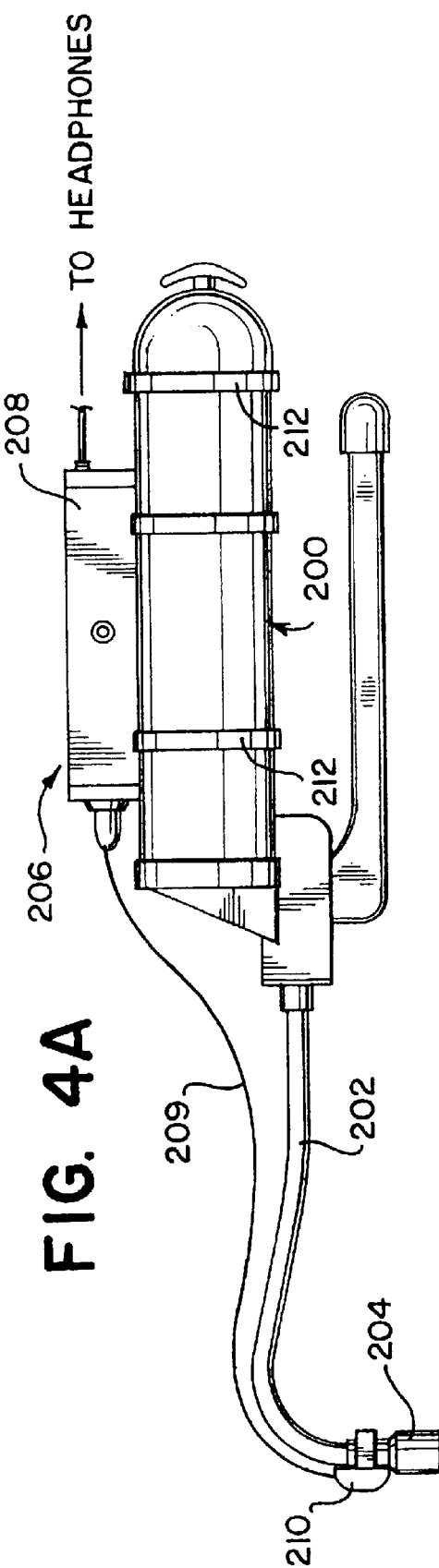
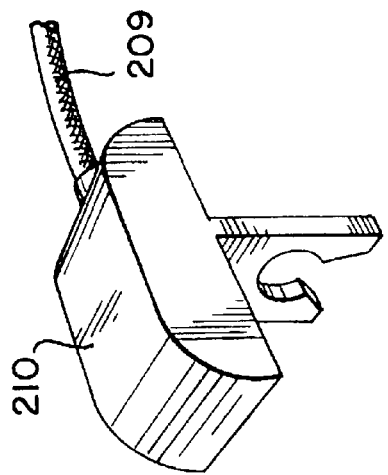
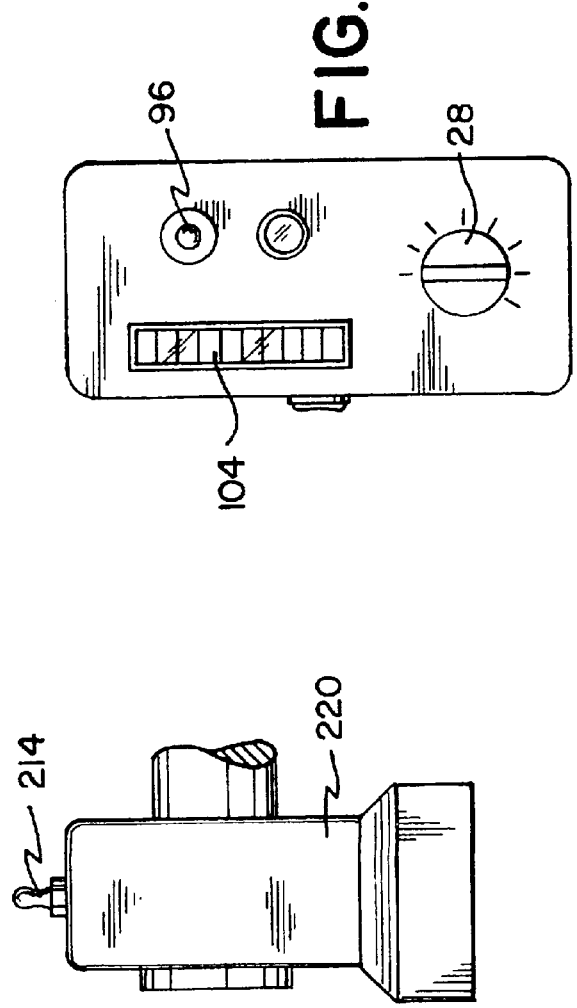

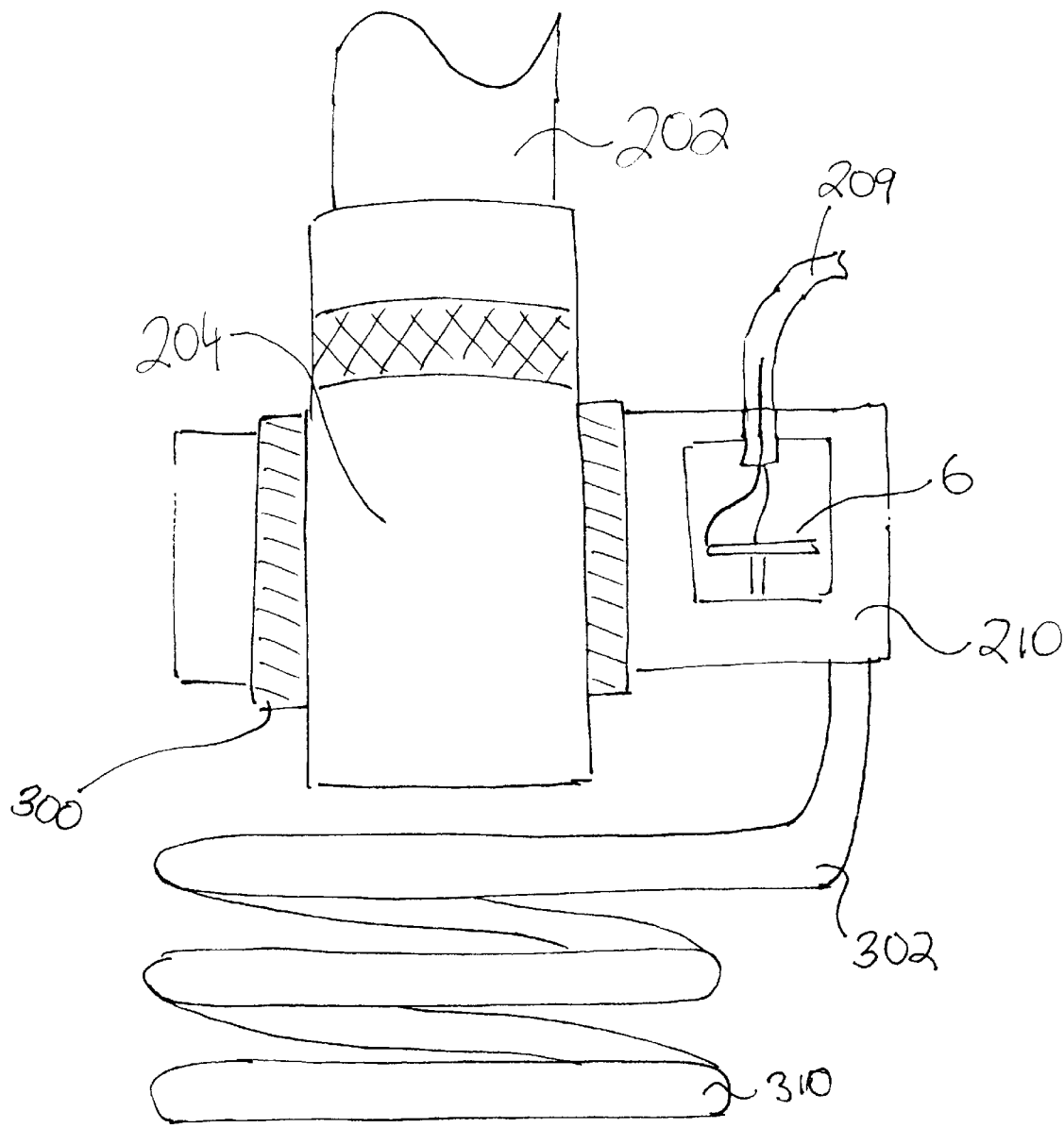
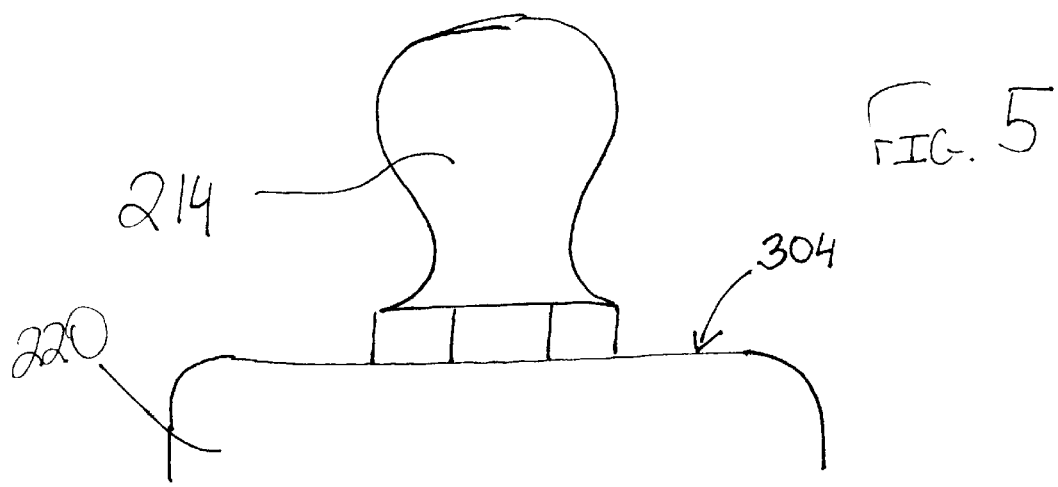
FIG. 5

ULTRASONIC DETECTING LUBRICATION APPARATUS WITH ACOUSTICALLY ISOLATED TRANSDUCER

STATEMENT OF RELATED APPLICATIONS

This application is a Continuation-In-Part of U.S. application Ser. No. 09/028,554, filed on Feb. 24, 1998 and entitled "Ultrasonic Detecting Lubrication Apparatus and Method of Use", which is a Divisional of U.S. Ser. No. 08/749,910, now U.S. Pat. No. 5,955,670, filed on Nov. 15, 1996 and entitled "Ultrasonic Leak Detecting Apparatus".

BACKGROUND OF THE INVENTION

1. Field of the Invention

The invention pertains to an ultrasonic detector and more specifically to a light weight, battery-operated, precision instrument for detecting ultrasonic sound or vibrations, which is useful in detecting leaks and malfunctions.

2. Prior Art

It is well known that ultrasonic generators and detectors can be used to locate leaks or defects, e.g. in pipes. Such a system is shown in U.S. Pat. No. 3,978,915 to Harris. In that arrangement, ultrasonic generators are positioned in a chamber through which the pipes pass. At the ends of these pipes, exterior to the chamber, ultrasonic detectors are located. At the point where a leak occurs in the pipe or the pipe wall is thin, the ultrasonic energy will enter the pipe from the chamber and travel to the end of the pipe where the detector is located. The detector will receive an ultrasonic signal at the end of the pipe indicating the existence of the leak or weak spot in the pipe.

Ultrasonic sensors have also been used to detect ultrasonic energy generated by friction within mechanical devices as disclosed in U.S. Pat. No. Re. 33,977 to Goodman, et al. The greater the amount of friction, the greater the intensity of the generated ultrasonic energy. Applying a lubricant to the device reduces friction and consequently the intensity of the generated ultrasound drops. Measuring ultrasonic energy thus provides a way to determine when lubrication has reached the friction generating surfaces. Additionally, faulty devices such as bearings generate a higher level of ultrasonic energy than do good bearings, and thus this condition can also be detected. However, conventional means require two people to perform this procedure—one person to apply the lubricant to the device, and one person to operate the ultrasonic detector.

Since ultrasonic energy used for these purposes is generally in the range of 40 kHz, it is too high in frequency to be heard by a human being. Thus, means are typically provided for heterodyning or frequency shifting the detected signal into the audio range, and various schemes are available for doing this.

By locating an ultrasonic generator in a closed chamber, a standing wave pattern with peaks and nodes is established. If a node occurs at the position of a leak or weak spot, no ultrasonic energy will escape and the defect will not be detected. One method of addressing this problem is disclosed in U.S. Pat. No. Re. 33,977 to Goodman, et al. Goodman teaches varying the frequency of the applied ultrasonic energy so that the position of the nodes will shift over time so that a leak at a null or node will be detected. However, resort to this method adds complexity and expense to the testing hardware.

Ultrasonic transducers generally produce a low voltage output in response to received ultrasonic energy. Thus, it is necessary to amplify the detected signal using a high-gain preamplifier before it can be accurately processed. However, if low cost heterodyning and display circuitry are to be used, means must be made available to attenuate the amplified signal to prevent saturating these circuits when high input signals are present. This attenuation also adjusts the sensitivity of the device. For a hand-held unit, the degree of attenuation should be selectable by the user.

For example, U.S. Pat. No. 4,785,695 to Rose et al. discloses an ultrasonic leak detector with a variable resistor attenuator used to adjust the output level of an LED bar graph display. However, this attenuation method does not provide a way to establish fixed reference points to allow for repeatable measurements.

U.S. Pat. No. 5,089,997 to Pecukonis discloses an ultrasonic energy detector with an attenuation network positioned after an initial preamplifier and before the signal processing circuitry, which creates an audible output and an LED bar graph display. The resistors in the Pecukonis attenuation network are designed to provide an exponential relationship between the different levels of attenuation. However, Pecukonis does not heterodyne the detected signals to produce an audible output but rather teaches the benefits of a more complex set of circuits which compress a broad range of ultrasonic frequencies into a narrower audible range. For many applications, the cost and complexity of this type of circuitry is not necessary.

In addition to detecting ultrasonic sound escaping from a leak or defect, a detector using an acoustic transducer must be able to accurately locate the source that sound. To this end, conical sound collectors are used in conjunction with the transducer to increase its directionality as illustrated in U.S. Pat. No. 4,287,581 to Neale, Sr. However, conventional detectors do not utilize collection cones which are also specifically designed to provide additional input signal gain of an amount consistent with the units of measure provided by the detector.

When using ultrasonic energy to detect leaks, it is useful to have a portable ultrasonic sensor which indicates the presence and intensity of ultrasonic energy both visually and audibly. Goodman discloses an ultrasonic sensor which displays intensity of the detected signal on an output meter operable in either linear or logarithmic mode and also provides for audio output through headphones. U.S. Pat. No. 4,987,769 to Peacock et al. discloses an ultrasonic detector which displays the amplitude of the detected ultrasonic signal on a ten-stage logarithmic LED display. However, the detector disclosed in Peacock does not process the detected signal to produce an audible response, nor does it provide for signal attenuation after the initial pre-amplification stage.

SUMMARY OF THE INVENTION

The present invention is directed to providing a versatile, light weight, battery-operated, precision instrument for detecting ultrasound or vibration. The invention provides a wide dynamic range as well as fixed reference points through the entire range to provide for repeatable measurements. In one embodiment, the detector circuitry can be housed in a handheld unit used to detect leaks. In another embodiment, the detector can be used with a grease gun to detect whether a sealed mechanical device such as a bearing, gear box, or transmission has been properly lubricated and if the device is faulty.

In an illustrative embodiment of the invention, the ultrasonic detector has an acoustic or contact ultrasonic transducer for detecting ultrasonic sound and converting it into an electric signal whose amplitude and frequency reflect that of the detected sound. A removable focusing probe funnels ultrasound into the transducer so as to collect the ultrasonic energy and focus it on a single transducer crystal. Prior art devices may use a plurality of transducers placed on a focusing surface. However, there are nulls in the reception with such an arrangement. Thus, the probe eliminates the possibility of missing a leak caused by receiving and/or positioning nulls that occur with multi-transducer receiving transducer modules. This probe also provides an additional 10 dB of signal gain.

The output signal is passed through a high-gain preamp which has significant headroom so as to avoid saturation when large ultrasonic energy fields are detected. Further, the preamplifier is arranged as a charge amplifier so it will be relatively insensitive to changes in transducer output impedance or capacitance. The preamplifier's output is capacitively coupled to a logarithmic attenuator network in order to adjust for baseline or ambient noise levels and to prevent saturation of the output audio amplifier and display circuitry. The network provides fixed signal attenuation levels of 0 dB through −70 dB in −10 dB steps. A supplemental variable resistor is also provided to allow for additional attenuation when extremely high ultrasound intensity levels are present.

The attenuated signal is then fed into a heterodyning circuit where the ultrasonic frequency is shifted into the audible range, filtered and amplified. Heterodyning is achieved by commutating or multiplexing the inputs of a tuned audio frequency filter with a high frequency signal, then differentially filtering and amplifying the heterodyned audio output, which then drives the speaker output and bar graph display. This technique takes advantage of the differential inputs of the LM386 audio amplifier to provide additional carrier rejection as well as a doubled voltage swing.

The audio amplifier of the present invention provides a low impedance output so the heterodyned and amplified signal can be used to drive 8 or 16 ohm speakers or headphones at a fixed output level. This output may also be used as an input for signal processors or analyzers.

The audio amplifier also drives a logarithmic LED bar graph display. This display has ten bar segments calibrated at 3 dB per bar in order to provide an output display covering a 30 dB window. The use of the logarithmic attenuator in combination with the log output display converts the input signal to a decibel format. This combination also gives the detector a wide dynamic range of approximately 100 dB in 33⅓ fixed discrete steps. These steps provide a set of fixed, repeatable reference points anywhere within the display range of the instrument. An additional 10 dB of dynamic range can be obtained by removing the focusing probe if necessary.

In a second embodiment, the detector is attached to a lubrication tool such as a grease gun for use in detecting when a mechanical device has been properly lubricated. When dealing with sealed bearings, for example, there is normally no way to know when the proper amount of lubricant has reached the friction areas, such as the raceway and the ball bearings. Too much grease can build up the internal pressure in the bearing and cause damage or can "blow" the seal, allowing contaminants to get into the bearing. Too little grease can cause the bearings to overheat and seize due to excess friction. The same is true for other sealed mechanical devices such as gear boxes or transmissions. Ultrasonic energy can be detected directly via the grease gun coupling. Alternatively, the ultrasonic transducer can be attached to the grease gun coupling but acoustically isolated from it and provided with a separate acoustic waveguide for transmitting ultrasonic energy from the sealed device directly to the transducer assembly.

Devices such as sealed bearings, gear boxes or transmissions generate ultrasonic energy when in use as a result of internal friction. As lubrication is applied, the internal friction is reduced. Consequently, the intensity of the generated ultrasound is lower. Measuring the level of ultrasound generated by the device as it is lubricated thus provides a way to determine when enough lubricant has been applied.

Additionally, devices such as sealed bearings generate higher than normal levels of ultrasound when they begin to fail. Because of the detector's fixed, repeatable reference points and wide dynamic range, the amount of ultrasound a specific lubricated bearing generates can be precisely measured and compared to a base line level. The degree to which the measured level exceeds normal indicates how badly the bearing has degraded.

Attaching the detector to a lubrication tool such as a grease gun has the further advantage of allowing the lubrication and ultrasound measurement procedures to be performed by one person, instead of the two required when conventional means are used.

BRIEF DESCRIPTION OF THE DRAWINGS

The foregoing and other features of the present invention will be more readily apparent from the following detailed description and drawings of illustrative embodiments of the invention in which:

FIG. 3A is an axial view of a removable ultrasonic focusing probe;

FIG. 3B s a lateral cross-sectional view of the focusing probe of FIG. 3A along line A–A';

FIG. 4A is an illustrative embodiment of the detector coupled with a grease gun;

FIG. 4B is a perspective view of the clip-on transducer housing;

FIG. 4C is a view of the control panel of one embodiment of the detector illustrating the LED display and attenuation selection switch;

FIG. 5 is an illustration of the detector coupled with a grease gun according to a second embodiment

DETAILED DESCRIPTION OF THE PREFERRED EMBODIMENTS

Figure 1:
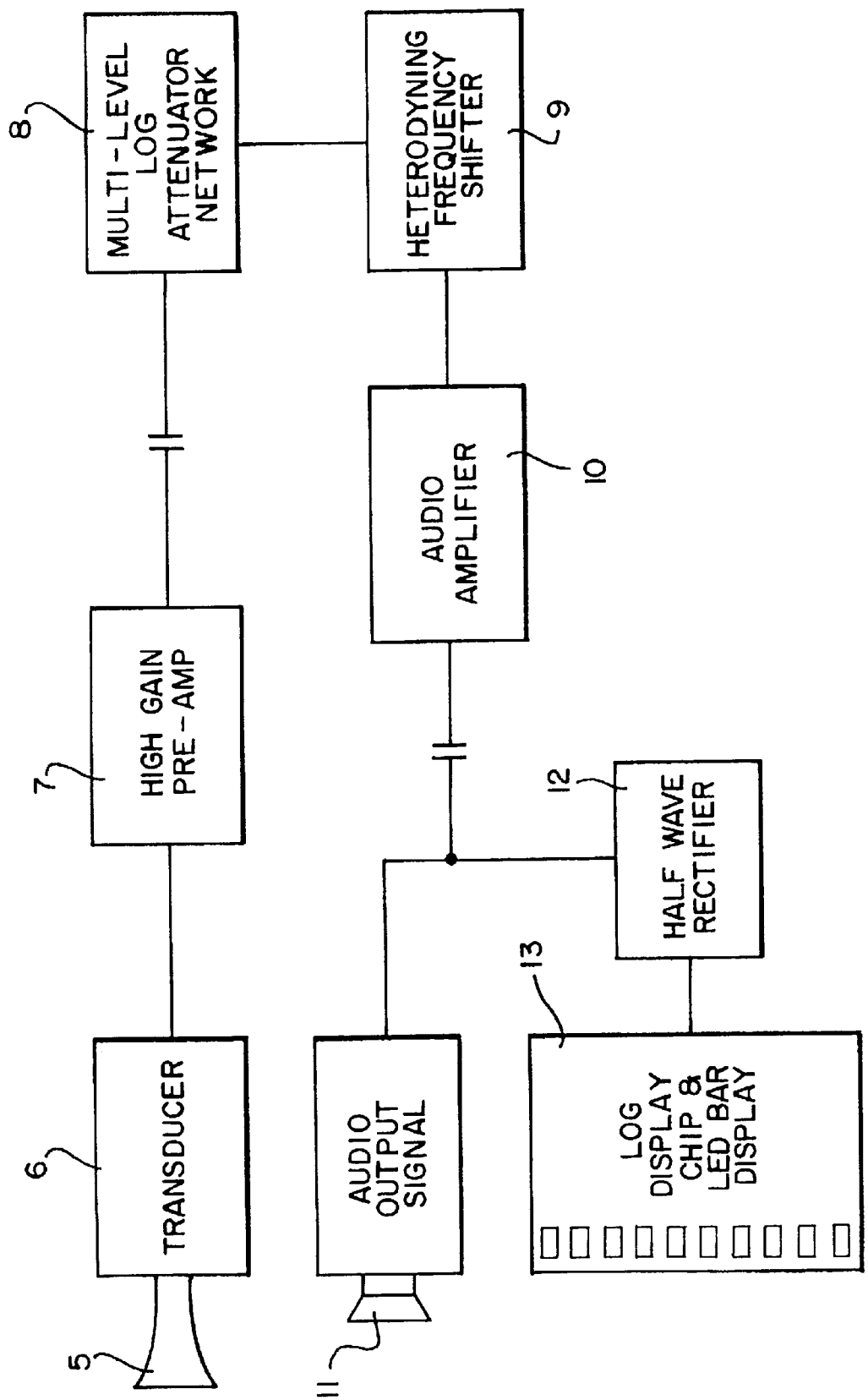
FIG. 1 is a block diagram of the present invention illustrating the arrangement of the circuit elements.

FIG. 1 shows a block diagram of one embodiment of the present invention. As illustrated in FIG. 1, ultrasonic energy is concentrated in the removable focusing probe 5 and applied to the ultrasonic transducer 6 to create an electronic signal whose amplitude and frequency represents that of the detected ultrasonic energy. Note that the transducer can be either an acoustic or a contact transducer, depending on the user's needs.

The output of the transducer 6 is fed into a high-gain preamp 7. The amplified input signal is then capacitively coupled to attenuator network 8 which attenuates the amplified input signal by one of several fixed logarithmic amounts according to the user's selection.

The attenuated signal is then fed into heterodyning frequency shifter 9 which generates an output signal of audible frequency and amplitude proportional to the ultrasonic frequency components of the applied signal. This output signal is amplified by audio amplifier 10 and supplied to low impedance output 11 where it can be used to drive speakers or headphones at a fixed output level and also may be used as an input for signal processors or analyzers. The amplified audio signal is also fed through a half-wave rectifier 12 then used to drive logarithmic display 13 which may be an LED bar graph display.

The individual circuit elements according to a preferred embodiment of the invention will now be described in more detail. All components used can have standard commercial temperature ranges and are off-the-shelf type items. The circuits are preferably driven from a battery with a voltage supply Vb ranging from 7.2 to 9 volts DC. The preferred embodiment may be constructed using a hybrid of surface mount and conventional thru hole components.

Figure 2A:
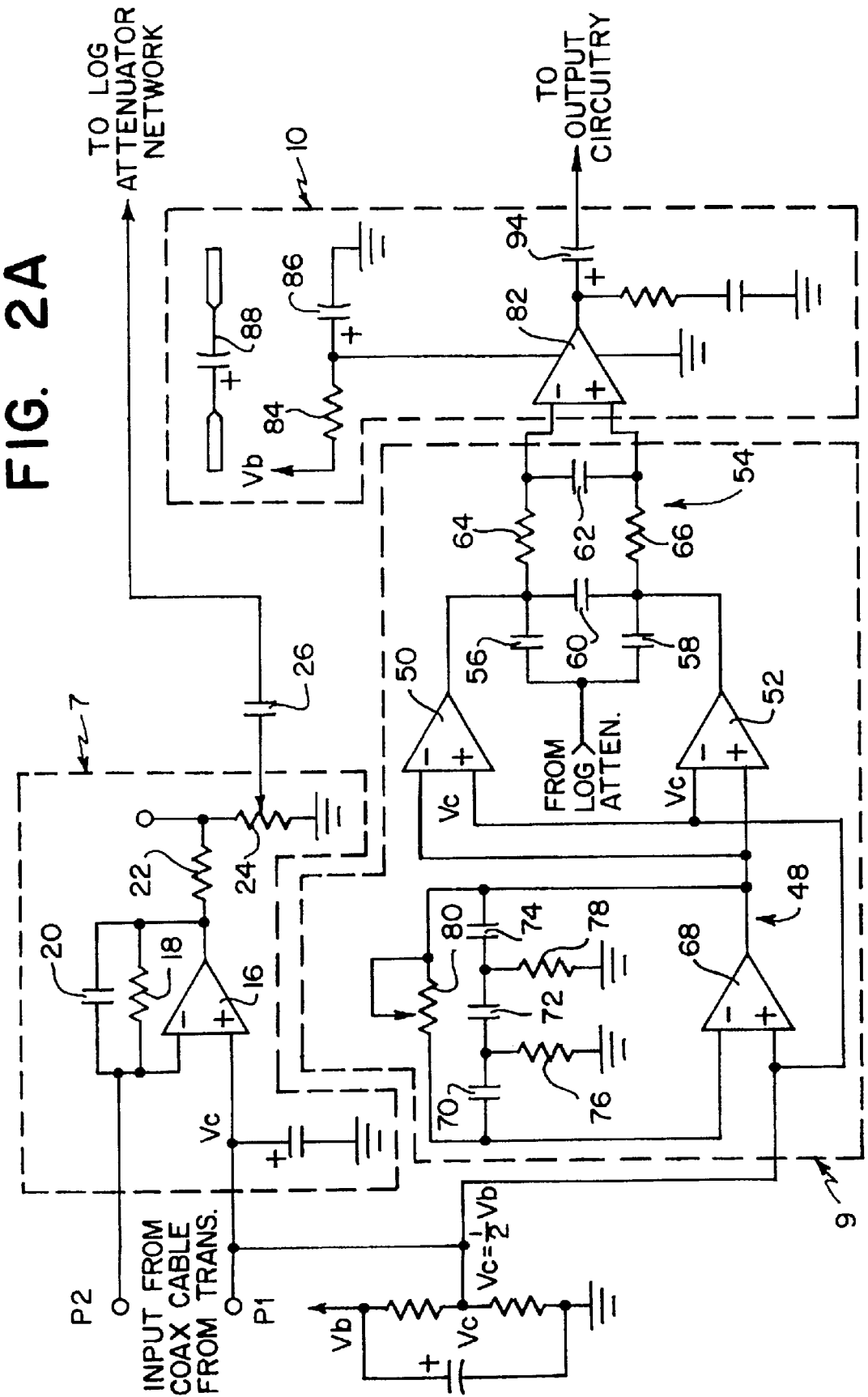
FIGS. 2A and 2B form a schematic diagram of a preferred embodiment of the present invention.

As seen in FIG. 2A, preamp 7 comprises an op-amp 16 with a parallel RC negative feedback loop comprising resistor 18 and capacitor 20. The non-inverting input of op amp 16 is biased to voltage Vc which is approximately half of supply voltage Vb from the battery. This amplifier configuration is classified as a charge amplifier because there is no series resistor between the transducers and the inverting input of the op amp 16. As a result, the signal from the transducers will send a charge in capacitor 20. The use of this type of amplifier makes the ultrasonic detector relatively insensitive to changes in transducer output impedance or capacitance. Also included as part of the output of preamp 7 is a supplemental attenuation circuit comprised of resistor 22 and variable resistor 24. Variable resistor 24 is normally set to provide no attenuation. Under extremely high ultrasound intensity levels, however, it can be adjusted to prevent the overdriving of the audio output to the speakers and display when the attenuator network 8 is set at maximum attenuation.

In the preferred embodiment, op amp 16 is a high gain IC amplifier such as an NE5532 chip. Resistor 18 is 1 Mohm and capacitor 20 is 4 pF. This results in a preamplifier having a gain of about 600 v/v or 55 dB with a bandwidth of 20 KHz to 100 KHz and an amplitude of approximately 6 volts peak-to-peak. This provides a sufficiently large amount of headroom to avoid most saturation problems. Given the typical transducer output voltage level of 100 to 200 microvolts, it would require an input of 10 millivolts from the transducer to produce the 6 volt output level. This headroom also allows the attenuator to be placed after the preamp 7.

Figure 2B:
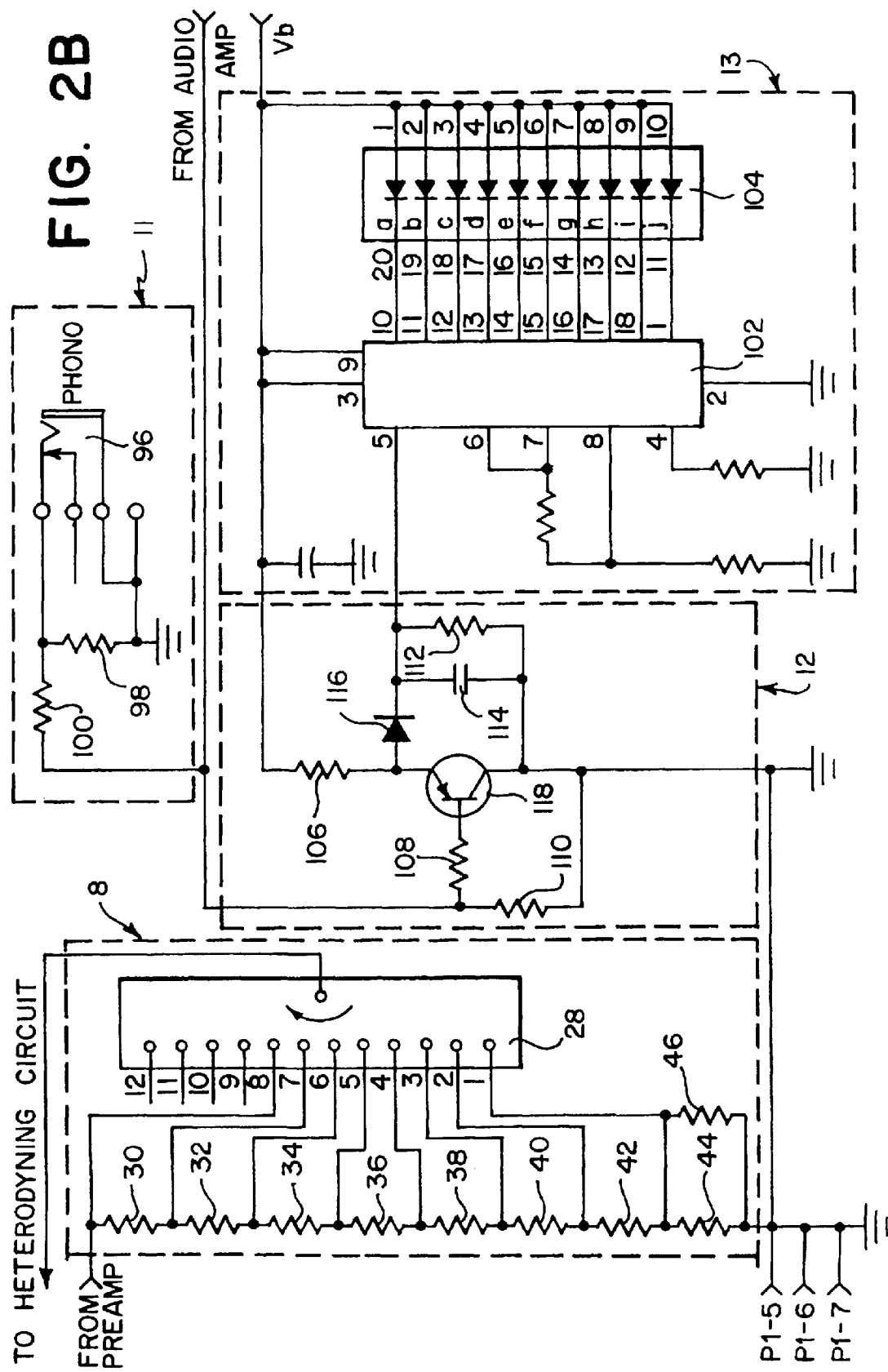

The output of preamp 7 is coupled through capacitor 26 to the log attenuator network 8 which is shown in FIG. 2B. Log attenuator network 8 comprises a multi-position switch 28 connected to series resistors 30, 32, 34, 36, 38, 40, 42, and 44. The values of the resistors are chosen to give the desired levels of attenuation, such as –10 dB per step. The amount of attenuation is a function of the ratios of resistance values and the interaction of the attenuator resistances and the input impedance of the heterodyning frequency shifter 9.

One method of determining the proper resistance values is to use a white noise source as an ultrasonic input signal. White noise is used because it characterizes ultrasonic leak and friction signals under turbulent flow conditions. The resistive values can then be adjusted while monitoring the output signal at different switch settings until the desired attenuation is achieved.

In the preferred embodiment, resistors 30, 32, 34, 36, 38, 40, and 42 are all of 1% tolerance and have values of 1.30K, 3.83K, 8.98K, 845, 140, 30.1, and 10 ohms respectively. Resistor 44 is 2.2 ohms with a 5% tolerance. In this configuration, the user can select between attenuation levels of from 0 dB to –70 dB in –10 dB intervals.

The attenuator network 8, like attenuator 24, is positioned after the high gain preamp 7 to prevent saturation of the audio output amplifier 10 and the overdriving of the output display 13. The output of the attenuation network is then fed to the heterodyning frequency shifter 9 and the audio amplifier 10 as shown in FIG. 2A.

The heterodyning frequency shifter 9 is comprised of a phase shift oscillator 48 which generates a commutating or switching signal, comparators 50 and 52, and tuned audio filter 54. The heterodyning circuit can be summarized as follows. Phase shift oscillator 48 includes op amp 68 and an RC feedback network made up of capacitors 70, 72, 74, resistors 76, 78 and variable resistor 80. The non-inverting input of op amp 68 is biased to voltage Vc in the same fashion as op amp 16. Circuit components are chosen so the oscillator operates at a frequency of approximately 37.2 kHz with an output varying around voltage Vc.

In the preferred embodiment, op amp 68 is a high gain integrated circuit such as an NE5532 chip. Capacitors 70, 72, and 74 are 560 pF each. Resistors 76 and 78 are each 1 Kohm and variable resistor 80 is 1 Mohm.

The commutating signal from the output of op amp 68 is applied to the inverting input of comparator 50 and the non-inverting input of comparator 52. The non-inverting input of comparator 50 and the inverting input of comparator 52 are biased to voltage Vc. The comparators must have open collector outputs, such as are present in an LM339 IC chip.

The audio amplifier 10 comprises op amp 82, which can be an LM386 IC, and associated resistor 84, capacitors 86 and 88.

The tuned audio filter 54 includes capacitors 60 and 62, and resistors 64 and 66. In the preferred embodiment, capacitor 60 is 0.01 uF, capacitor 62 is 0.047 uF, and resistors 64 and 66 are both 1 Kohm.

Heterodyning to shift the frequency of the detected ultrasonic signal into the audio range is achieved by commuting the inputs of the tuned audio frequency filter 54 at the high frequency of 37.2 kHz and then differentially filtering and applying the output to audio amplifier 10. The ultrasonic input signal is applied to the inputs of the tuned audio filter 54 through capacitors 56 and 58. On alternate half-cycles, the outputs of comparators 50 and 52 commutate the ultrasonic signal going to the differential inputs of op amp 82. Common mode rejection of op amp 82, combined with the filtering action of filter 54 extract the heterodyned audio which appears at the output of op amp 82. The extracted audio is coupled to the output circuitry through capacitor 94. In the described embodiment, the bandwidth of the heterodyning circuitry 9, 10 is approximately 0 to 20 kHz as compared to the bandwidth of 20 KHz to 100 kHz of the preamp circuit 7.

The output circuitry is depicted in FIG. 2B and comprises low impedance audio output 11 and a log LED display 13. The audio output 11 includes phono jack 96 and resistors 98 and 100. It is suitable for driving 8 or 16 ohm speakers or headphones at a fixed output level and is also suitable as an input for signal processors or analyzers.

In the preferred embodiment, the log display has a log response LED driver chip 102, such as the NSC 3915 log chip, which is used to drive a 10-segment LED bar display 104. The NSC 3915 is a proven low-cost device and is accurate and efficient for these purposes.

The log display circuitry 13 is driven by a half-wave rectifier 12 made up of resistors 106, 108, 110, and 112, capacitor 114, diode 116, and transistor 118. Rectifier 12 rectifies the heterodyned, log attenuated audio signal and feeds it to the log display chip 102 as an average value signal.

As can be seen, the use of the log attenuator in combination with the log output display converts the input signal to decibel display format. The 8 positions of the attenuator provide both a wide dynamic range and fixed reference points, i.e., each switch position provides fixed known amounts of attenuation. Variable potentiometers cannot provide this type of accuracy. For example, if two signals of very different amplitude are to be compared, the attenuator can be used to reduce the larger signal's amplitude range or increase the smaller's, and they then can be accurately measured or compared. The difference between the range of the larger and smaller signals' amplitude ranges will be known from the amount of attenuation needed, as evidenced by the switch position. The use of fixed reference points (used to determine base line or ambient noise levels) gives this sensor the flexibility to be used as a precision instrument and to provide repeatable measurements.

Additional accuracy and flexibility can be achieved through the use of a conical-shaped removable focusing probe 5 shown in FIGS. 3A and 3B. Use of probe 5 as a front end to the ultrasonic transducer 6 increases directivity and adds an additional 10 db through 12 dB of signal gain. The focusing probe 5 also funnels ultrasound into the single transducer 6. This funneling action reduces the chance that the user will miss a leak caused by receiving and/or positioning nulls that occur when using multi-transducer receiving transducer modules.

In an alternative embodiment, shown in FIG. 4A, the ultrasonic detector 206 can be connected to a lubrication tool such as grease gun 200 which has a neck 202 and a grease fitting adaptor 204. The ultrasonic circuitry is housed in casing 208 which is attached to the body of grease gun 200 by Velcro™ straps 212. Alternatively, casing 208 can be attached to grease gun 200 by clips, wire ties, or any other suitable means, such as welding and adhesives.

Ultrasonic transducer 6 (not shown) is contained within housing 210 and connected to the ultrasonic circuitry by wire 209. Transducer housing 210 attaches to grease gun 200 along neck 202 near grease fitting adaptor 204 or to adaptor 204 itself. One embodiment for transducer, housing 210, a clip-on variety, is illustrated in FIG. 4B. Note, however, that transducer 6 can be attached by any other mechanism that places it in acoustical contact with grease fitting adaptor 204 or neck 202. Other ways to attach the transducer to the grease gun include by a strap or magnetically. Alternatively, neck 202 or grease fitting adaptor 204 can be specially constructed with means to securely receive a suitably shaped housing 210.

When a mechanical device is in use, internal friction results in the generation of ultrasound. As lubrication is applied and reaches the friction or ultrasound generating surfaces, the intensity of the generated ultrasound is reduced. Coupling an ultrasonic detector with a lubrication tool such as a grease gun allows a single user to apply lubrication to a mechanical device while simultaneously monitoring the intensity of ultrasonic energy generated by that device. This allows the user to see when the detected ultrasonic energy drops to its lowest level, and thus when enough lubrication has been applied.

In one use for this embodiment, grease gun 200 can be used to lubricate sealed bearing 220. Because bearing 220 is sealed, there is normally no way to know when the proper amount of grease has reached the friction areas, such as the raceway and the ball bearings. Too much grease can build up the internal pressure of the bearing and cause damage or can "blow" the seal, allowing contaminants to get into the bearing. Too little grease can cause the bearings to overheat and seize due to excess friction. A similar problem occurs when lubricating other sealed mechanical devices such as gear boxes or transmissions.

In use, grease fitting adaptor 204 attaches to grease fitting 214 on bearing 220. Grease fitting adaptor 204 then acts as a wave guide, transmitting the ultrasound generated by sealed bearing 220 to transducer 6. As lubricant is applied, the level of ultrasound generated by bearing 220 is indicated visually on LED bar display 104 and audibly through headphones (not shown) connected to phono jack 96. See FIG. 4C. As shown in FIG. 4C, using the fixed attenuation setpoints selectable by attenuator switch 28 and by monitoring LED bar graph display 104 on the control panel of the unit, the drop in the level of detected ultrasonic energy can be precisely measured.

Lubrication is packed into bearing 220 until the detected level of ultrasound reaches its lowest level, an indication that enough lubricant has been applied. Since the detector can precisely measure the differences in amplitude of the ultrasonic signal, the user has the ability to prevent the bearing from being "over packed" and consequently blowing out the seal.

In an alternative embodiment, illustrated in FIG. 5, the transducer housing 210 containing transducer 6 is mounted to or near the grease fitting adaptor 204 but is acoustically isolated from the grease fitting adaptor 204, e.g., by placing a layer of acoustic absorbent material 300 between the adaptor 204 and the housing 210. The material 300 should absorb acoustic energy at least in the range detected by the transducer 6. In a preferred embodiment, the material 300 is rubber, either natural or artificial. It has been found that a layer of rubber having a thickness on the order of ⅛ inch or more absorbs sufficient ultrasonic energy to effectively acoustically isolate transducer housing 210 (and thereby the transducer) from the adaptor 204.

Attached to the transducer housing 210 is an acoustic waveguide 302, such as a metal spring or "foot", which is configured to make acoustical contact with a top surface 304 of the bearing housing 220 when the adaptor 204 is coupled to the fitting 214. Acoustic energy is carried by the waveguide 302 from the bearing 220 to the transducer housing 210.

Figure 6:
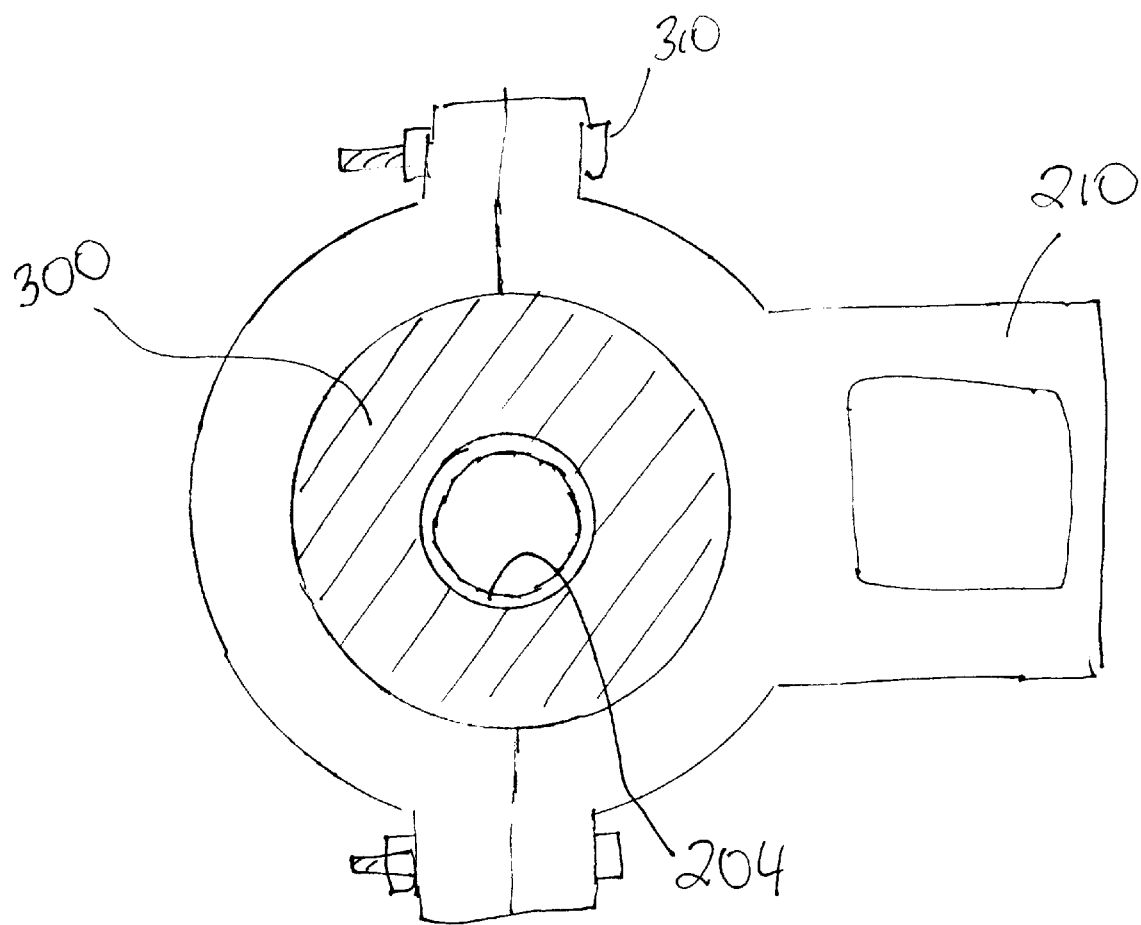
FIG. 6 is a cross sectional view of one arrangement of the embodiment of FIG. 5.

There are various ways in which the transducer 210 can be attached to the adaptor 204 in an acoustically isolated manner. In one embodiment, a clip-on housing 210 (such as shown in FIG. 4B) can be modified to include a layer of acoustic absorbent material 300 on the inner portion of the clip. In an alternative arrangement, such as shown in the cross-sectional view of FIG. 6, the acoustic absorbent material 300 and transducer housing 210 can encircle the adaptor 204. In this arrangement, the acoustically isolated transducer assembly can be provided separately from the grease fitting adaptor 204 and be sized to slide on to the adaptor 204 and retained in place via friction or the housing 210 can be provided in separate parts which are clamped around the material 300, e.g., with clamping screws 310. Advantageously, in this embodiment, the material 300 can be formed of conventional rubber tubing which is widely available in many sizes. Other configurations are also possible, as will be recognized by those of skill in the art. For example, the entire transducer housing can be formed of an acoustically absorbent material, such as rubber, so that a separate layer of acoustically absorbent material is not needed.

Figure 7:
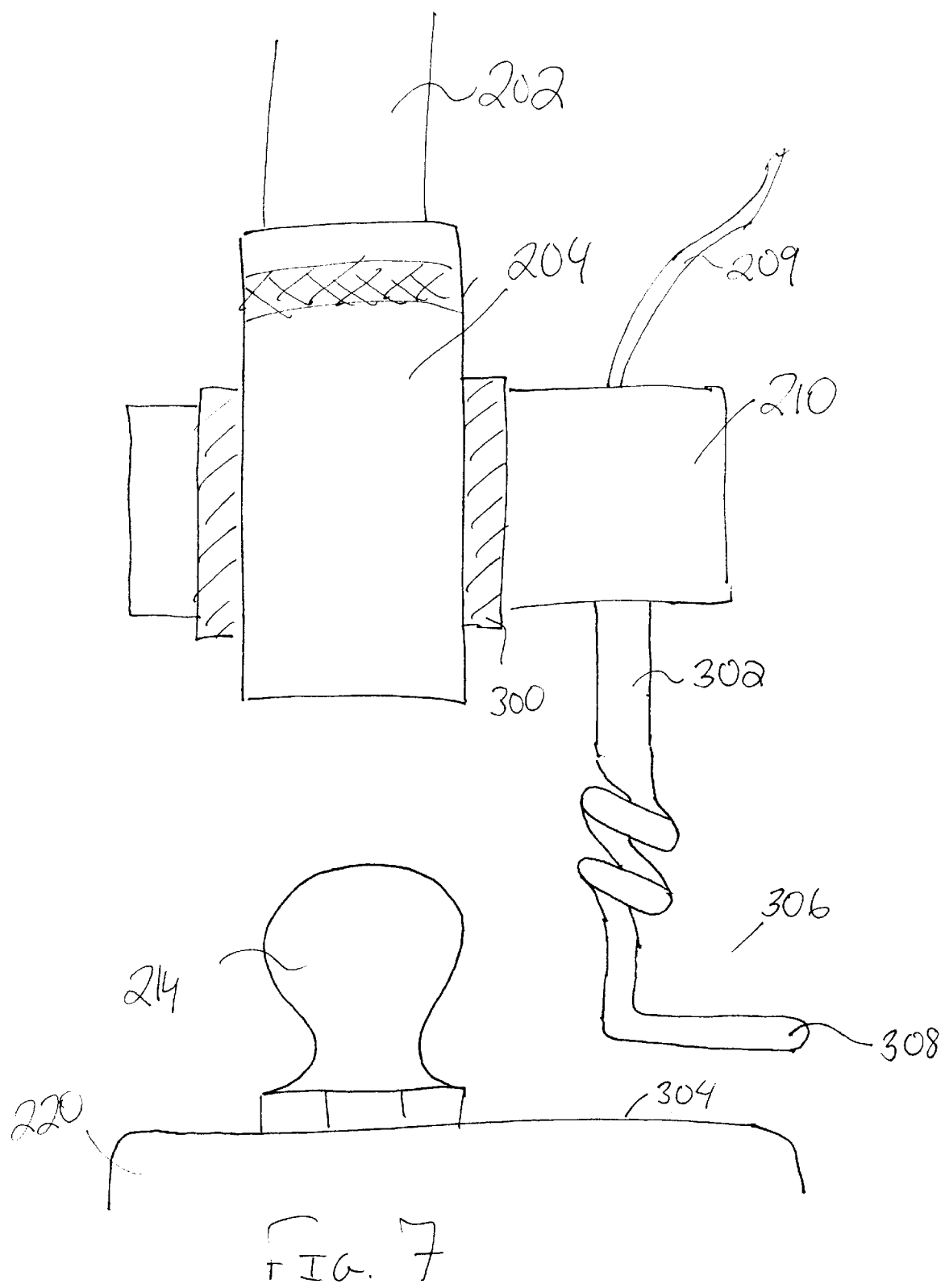
FIG. 7 is an illustration of the detector coupled with a grease gun according to the second embodiment and having a modified acoustic waveguide.

Various configurations for the acoustic waveguide 302 are also possible. Preferably, the waveguide 302 bendable so that a firm acoustic contact will be made with the top surface 304 of the bearing 220 when the adaptor 204 engages the fitting 214. In the embodiment shown in FIG. 5, the waveguide 302 has at least one loop 310 which is greater than the diameter of the adaptor 204 so that the adaptor 204 will pass through the loop 310 when engaged. In another configuration, shown in FIG. 7, the body of the waveguide 302 is positioned adjacent the adaptor 204 and provided with a foot 308 for making acoustic contact with the surface 304 of the bearing 220. The shape of the foot can be of any suitable configuration. For example, foot 308 can be spit to form a "Y" shaped configuration and positioned so that arms of the Y will surround the adaptor 204 and fitting 214 when the assembly is engaged.

Advantageously, this alternative embodiment does not require that the adaptor fitting 204 be suitable for carrying ultrasonic energy or require that good acoustical connection be established between the fitting 204 and the fitting 214 on bearing 220. In addition, because the transducer is acoustically isolated from the adaptor 204, the transducer will not detect ultrasonic energy which is carried through the components of the grease gun. Thus, the system is insensitive to ultrasonic energy which may be present in the grease gun from other sources besides the particular bearing being greased, such as energy introduced by another mechanical device in contact with a portion of the grease gun.

Either grease-gun embodiment can be used to detect faulty bearings. In use, good bearings generate a normal base level of ultrasonic energy. When measured, this energy level corresponds to a specific position of the log attenuator switch 28 and a certain number of lit bars on LED display 104. This level can be determined, for example, by attaching grease gun 200 to a properly lubricated bearing known to be in good condition, and then measuring the detected ultrasound. The fixed reference points ensure that this measurement is repeatable and allow the value to be used as a reference or baseline when subsequent measurements are made.

In practice, an operator attaches grease fitting adapter 204 of grease gun 200 to grease fitting 214 on bearing 220 and then measures the intensity of emitted ultrasound. If the detected level is higher than the predetermined base level, lubrication can be applied until the detected ultrasound level reaches its lowest level. However, even after a faulty bearing is lubricated, it will still produce a higher level of ultrasound than normal. The number of decibels above the base line reading indicates the stage of failure the bearing is in.

A reading of 8 dB above baseline indicates that the bearing is in a pre-failure stage, the earliest stage of failure. In this stage, the bearing may have developed flaws not visible to the human eye, such as hairline cracks or microscopic spalls. Because of the fixed reference points and the 3 dB per bar scale of the LED bar display, even this small increase in generated ultrasonic energy can be accurately detected.

A reading of 16 dB above baseline indicates that the bearing is at failure stage. At this level, the bearing should be replaced or frequently monitored. When the detected level of ultrasound is 35–50 dB above normal, the bearing is at a catastrophic stage and rapid failure is imminent. This is a highly dangerous condition since the bearing clearances increase and cause additional friction and rubbing within a machine, thus causing potential damage to other components.

Note that while the prior discussion addressed using one embodiment of the invention to lubricate and test a sealed bearing, this embodiment can also be used with other sealed mechanical devices such as gear boxes and transmissions for the same purposes.

While the invention has been particularly shown and described with reference to preferred embodiments thereof, it will be understood by those skilled in the art that various changes in form and details may be made therein without departing from the spirit and scope of the invention.

What is claimed:

1. An apparatus for detecting ultrasonic energy generated by a mechanical device and for applying lubricant to said device, said apparatus comprising:
   a lubrication tool having a lubrication delivery element;
   an ultrasonic transducer which is attached to the lubrication delivery element and is acoustically isolated therefrom;
   an acoustical waveguide in acoustical contact with the transducer and configured to make acoustical contact with the device when the lubrication tool is applied to the device, the transducer producing an electrical signal with an intensity related to the intensity of ultrasonic energy received from the acoustical waveguide; and
   an electrical circuit for processing said electrical signal and having an output indicating the magnitude of said electrical signal.

2. The apparatus of claim 1, wherein:
   said lubrication tool comprises a grease gun; and
   said lubrication delivery element comprises a grease fitting adaptor suitable for interfacing with said mechanical device.

3. The apparatus of claim 2, further comprising a transducer housing containing the transducer.

4. The apparatus of claim 3, further comprising a layer of acoustic absorbent material interposed between the transducer housing and the grease fitting adaptor.

5. The apparatus of claim 4, wherein the layer of acoustic absorbent material comprises a layer of rubber having a thickness of at least substantially one eight inch.

6. The apparatus of claim 4, wherein the acoustical waveguide comprises a body depending from the transducer housing and terminating in a foot configured to make acoustical contact with the device when the lubrication tool is applied to the device.

7. The apparatus of claim 6, wherein, when the lubrication tool is applied to the device, the foot is adjacent to the grease fitting adaptor.

8. The apparatus of claim 6, wherein the foot is generally Y-shaped.

9. The apparatus of claim 2, wherein the acoustical waveguide comprises a metal spring having at least one loop with a diameter greater than a diameter of the grease fitting adaptor, wherein the grease fitting adaptor will pass through the loop when the lubrication tool is applied to the device.

10. The apparatus as claimed in claim 1, wherein said circuit comprises:

a high gain preamplifier connected to said electrical signal from the transducer, said preamplifier generating an amplified version of the electrical signal;

a multi-level logarithmic attenuator receiving the output of the preamplifier, said logarithmic attenuator creating an attenuated version of the output signal of said preamplifier with at least one fixed reference point; and a signal level indicator connected to receive the attenuated signal and to provide an indication of the magnitude of the detected ultrasonic energy.

11. The apparatus as claimed in claim 10, wherein said multi-level logarithmic attenuator comprises selectable fixed attenuation levels of 0 dB to −70 dB in −10 dB steps.

12. The apparatus as claimed in claim 10, wherein said signal level indicator comprises a logarithmic display circuit and an LED bar display driven by said logarithmic display circuit.

13. The apparatus as claimed in claim 10, wherein said signal level indicator comprises:

a frequency shift circuit connected to receive the output of the logarithmic attenuator, said shift circuit producing an audio frequency range signal related in magnitude and frequency to the attenuated signal, but shifted from the ultrasonic frequency range to an audio frequency range; and an audio amplifier which receives the audio signal from the frequency shift circuit and amplifies it to create an amplified audio output signal.

14. An ultrasonic transducer assembly for use with apparatus for detecting ultrasonic energy generated by a mechanical device and for applying lubricant to said device, the assembly comprising:

an ultrasonic transducer;

a transducer housing containing the transducer and comprising a layer of acoustic absorbent material adjacent at least a portion of the transducer; and an acoustical waveguide in acoustical communication with the transducer;

wherein when the transducer assembly is connected to the apparatus, the acoustic absorbent material is interposed between the transducer housing and the apparatus to acoustically isolate the transducer from the apparatus.

15. The assembly of claim 14, wherein the layer of acoustic absorbent material comprises a layer of rubber having a thickness of at least substantially one eight inch.

16. The assembly of claim 15, wherein the layer of acoustic absorbent material comprises rubber tubing having a diameter sufficient to receive a portion of the apparatus.

17. The assembly of claim 14, wherein the acoustical waveguide comprises a spring depending from the transducer housing.

18. The assembly of claim 14, wherein the acoustical waveguide comprises a body depending from the transducer housing and terminating in a foot configured to make acoustical contact with the device when the apparatus is applied to the device.

19. The apparatus of claim 18, wherein the foot is generally Y-shaped.

20. The apparatus of claim 14, wherein the apparatus is configured to be removably attached to the assembly.

21. An apparatus for use with a lubrication tool to detect ultrasonic energy generated by a mechanical device as lubricant is applied to the mechanical device, said lubrication tool having a body and a lubrication delivery element, said apparatus comprising:

an ultrasonic transducer which produces an electrical signal having an intensity related to the intensity of received ultrasonic energy;

a housing containing said transducer and being removably attachable to the outside of the lubrication delivery element, the housing being configured to acoustically isolate the transducer from the lubrication delivery element when the housing is attached to the lubrication delivery element;

an acoustical waveguide in acoustical contact with the transducer and configured to make acoustical contact with the device when the lubrication tool is applied to the device, the transducer producing an electrical signal with an intensity related to the intensity of ultrasonic energy received from the acoustical waveguide; and an electrical circuit for processing said electrical signal and having an output indicating the magnitude of said electrical signal.

22. The apparatus as claimed in claim 21, wherein:

said lubrication tool is a grease gun;

said lubrication delivery element comprises a grease fitting adaptor suitable for interfacing with said mechanical device; and said housing is removably attachable to the outside of said grease fitting adaptor.

23. The apparatus as claimed in claim 21, further comprising a casing containing said electrical circuit, said casing being removably attachable to the body of said lubrication device.

* * * * *